United States Patent [19]

Weyenberg et al.

[11] Patent Number: 5,614,230
[45] Date of Patent: Mar. 25, 1997

[54] APPARATUS FOR FORMING A CURL ON AN END OF A TUBULAR MEMBER

[75] Inventors: Jeffrey M. Weyenberg, Appleton; Allan J. Krueger, Winneconne; Noel J. Rasmussen, Oshkosh, all of Wis.

[73] Assignee: Kimberly-Clark Corporation, Neenah, Wis.

[21] Appl. No.: 366,074

[22] Filed: Dec. 29, 1994

[51] Int. Cl.⁶ .................................................. B28B 21/92
[52] U.S. Cl. ........................ 425/393; 425/402; 493/159; 493/454; 264/310
[58] Field of Search ................................. 493/158, 159, 493/454, 459; 425/392, 393, 402; 264/296, 310

[56] References Cited

U.S. PATENT DOCUMENTS

| | | | |
|---|---|---|---|
| 1,181,965 | 5/1916 | Bohlman | 493/158 |
| 2,178,840 | 11/1939 | Lorenian | 604/200 |
| 2,298,752 | 10/1942 | Crockford | 604/11 |
| 2,639,646 | 5/1953 | Thompson et al. | 493/158 X |
| 2,916,975 | 12/1959 | Gasior et al. | 493/158 X |
| 3,065,677 | 11/1962 | Loeser | 493/158 X |
| 3,078,025 | 2/1963 | Welshon | 229/400 |
| 3,087,390 | 4/1963 | Ruza | 493/158 X |
| 3,141,595 | 7/1964 | Edwards | 229/400 |
| 3,164,314 | 1/1965 | Waycie | 229/400 |
| 3,203,611 | 8/1965 | Anderson et al. | 229/403 |
| 3,204,635 | 9/1965 | Voss et al. | 604/14 |
| 3,312,383 | 4/1967 | Shapiro et al. | 229/400 |
| 3,347,234 | 10/1967 | Voss | 604/14 |
| 3,433,225 | 3/1969 | Voss et al. | 604/14 |
| 3,572,339 | 3/1971 | Voss et al. | 604/15 |
| 3,575,169 | 4/1971 | Voss et al. | 604/18 |
| 3,581,744 | 6/1971 | Voss et al. | 604/14 |
| 3,676,543 | 7/1972 | Reinhold et al. | 264/296 |
| 3,696,812 | 10/1972 | Jaycox | 604/18 |
| 3,805,786 | 4/1974 | Bernardin et al. | 604/14 |
| 3,807,399 | 4/1974 | Morman et al. | 604/14 |
| 4,104,013 | 8/1978 | Kelly et al. | 425/324.1 |
| 4,215,087 | 7/1980 | Mathison | 264/320 |
| 4,298,331 | 11/1981 | Mueller | 425/393 |
| 4,302,174 | 11/1981 | Hinzmann | 425/341 |
| 4,412,833 | 11/1983 | Wiegner et al. | 604/14 |
| 4,453,925 | 6/1984 | Decker | 604/14 |
| 4,479,791 | 10/1984 | Sprague | 604/14 |
| 4,508,531 | 4/1985 | Whitehead | 604/14 |
| 4,650,459 | 3/1987 | Sheldon | 604/15 |
| 4,778,374 | 10/1988 | Takahashi et al. | 425/343 |
| 4,846,802 | 7/1989 | Sanders, III | 604/15 |
| 5,184,995 | 2/1993 | Kuchenbecker | 493/79 |
| 5,279,541 | 1/1994 | Frayman et al. | 604/14 |
| 5,290,501 | 3/1994 | Klesius | 264/322 |

FOREIGN PATENT DOCUMENTS

| | | |
|---|---|---|
| 27595 | 10/1960 | Japan. |
| 1012217 | 12/1965 | United Kingdom. |
| 1484912 | 9/1977 | United Kingdom. |

Primary Examiner—Robert J. Warden
Assistant Examiner—E. Leigh Dawson
Attorney, Agent, or Firm—Thomas J. Connelly

[57] ABSTRACT

An apparatus is disclosed for forming a curl on an end of a tubular member. The apparatus includes first and second members. The first member is capable of holding the tubular member and has an external shoulder beyond which the first end of the tubular member extends a set amount. The second member is coaxially aligned with and is engageable with the first end of the tubular member. The second member includes a pilot which is sized to be inserted into the first end of the tubular member. The second member also includes a sleeve which surrounds the pilot and cooperates with the external shoulder when the second member engages the first end of the tubular member to form a curling chamber. The second member further includes a curling element positioned between the pilot and the sleeve which is capable of contacting the first end of the tubular member. The apparatus further includes means for rotating one of the members and means for moving the members into engagement. As the members engage, the curling element contacts the first end of the tubular member and forms a curl thereon within the confines of the curling chamber.

39 Claims, 3 Drawing Sheets

FIG. 10

APPARATUS FOR FORMING A CURL ON AN END OF A TUBULAR MEMBER

FIELD OF THE INVENTION

This invention relates to an apparatus for forming a curl on an end of a tubular member. More specifically, this invention relates to an apparatus for forming an outwardly extending, integral fingergrip ring on a tampon applicator.

BACKGROUND OF THE INVENTION

There are various kinds of applicators known today which can be utilized to dispense a product or substance into a body cavity or onto the skin of a human or an animal. A tampon applicator is specifically used to insert a catamenial tampon into a woman's vagina to absorb menstrual fluid, blood and other kinds of body fluid.

Tampon applicators are available in a variety of shapes and sizes. Some applicators are constructed of paper, paperboard or cardboard while others are made from plastic or are a laminate of two or more different materials. The applicator can be either a single member wherein the user utilizes her finger to expel the tampon or the applicator can be formed from two or more members which are telescopically assembled. A typical two piece applicator employs a hollow tube for housing the tampon and a second tube or plunger which interacts with the first tube to expel the tampon into a woman's vagina.

In using a one piece applicator, the user will normally hold and position the applicator tube approximate her vagina with her thumb and middle finger. She will then use her index finger to expel the tampon into her vagina. With the two piece applicator, the user will normally hold and position the outer tube of the applicator approximate her vagina with her thumb and middle finger. The inner tube is then pushed into the outer tube by movement of her index finger so as to expel the tampon into her vagina. After the tampon is expelled, the applicator is withdrawn and discarded. It has been found that it is much easier for a woman to control the placement of the outer tube into her vagina when a fingergrip ring is provided on either the inner and/or outer tubes.

An integrally formed fingergrip ring is preferred over a non-integral fingergrip since an integrally formed ring tends to be stronger in shear strength and simplifies manufacturing of the product. The fingergrip ring should be sized and configured to provide control of the applicator to ensure comfortable insertion of a tampon or other substance into a body cavity. Up until now, it has been very difficult to mass produce integrally formed fingergrip rings on tampon applicators, especially paper applicators, having a diameter of less than about 1.25 inches (about 31.75 mm). One reason for this is that paper which has been formed into a small diameter tubular member is very susceptible to being ripped or torn when it is subjected to a curling operation. Accordingly, the apparatuses taught in U.S. Pat. Nos. 1,181,965 and 3,065,677 do not work satisfactory because the frictional forces which are developed between the paper and the curling tool will literally destroy the product.

Now an apparatus has been invented for forming a curl on an end of a tubular member even when the tubular member is formed from paper and has a very small diameter.

SUMMARY OF THE INVENTION

Briefly, this invention relates to an apparatus for forming a curl on an end of a tubular member. The apparatus includes first and second members. The first member is capable of holding the tubular member and has an external shoulder beyond which the first end of the tubular member extends. The second member is coaxially aligned with the first member and is engageable with the first end of the tubular member. The second member includes a pilot which is sized to be inserted into the first end of the tubular member. The second member also includes a sleeve which surrounds the pilot and cooperates with the external shoulder when the second member engages the first end of the tubular member to form a curling chamber. The second member further includes a curling element positioned between the pilot and the sleeve which is capable of contacting the first end of the tubular member. The apparatus further includes means for rotating one of the members and means for moving the second member into engagement with the tubular member. When the curling element contacts the first end of the tubular member the curl is formed thereon within the confines of the curling chamber.

The general object of this invention is to provide an apparatus for forming a curl on an end of a tubular member. A more specific object of this invention is to provide an apparatus for forming an inwardly or an outwardly extending curl on a tubular member.

Another object of this invention is to provide an apparatus for forming a curl on an end of a small diameter, paper tube.

A further object of this invention is to provide an apparatus which can form an outwardly extending, integral curl on a tampon applicator which can serve as a fingergrip ring.

Still another object of this invention is to provide an apparatus which can curl an end of a tubular member quickly and efficiently.

Still further, an object of this invention is to provide an apparatus which can curl an end of a tubular member in a cost effective manner and at relatively high manufacturing speeds.

Other objects and advantages of the present invention will become more apparent to those skilled in the art in view of the following description and the accompanying drawings.

DETAILED DESCRIPTION OF THE PREFERRED EMBODIMENTS

Referring to FIGS. 1–4, an apparatus 10 for forming a curl on an end of a tubular member 12 is shown. By "tubular member" is meant a member having a cavity or opening 14 formed therein or therethrough with a wall 16 approximate the end which is to be curled. The wall 16 should be relatively thin. The cavity or opening 14 should extend to at least one outside surface thereof. The tubular member 12 can be cylindrical, non-cylindrical, conical, frusto-conical or of some other shape which is opened at one or more ends. The tubular member 12 does not have to have a uniform outside diameter although such a diameter is preferred for many articles.

Two articles which can be curled by the apparatus 10 include a cylindrical tube which is useful as a tampon applicator and a cylindrical tube which is useful as a medicinal applicator. A tampon applicator facilitates positioning of an absorbent tampon into a woman's vagina and a medicinal applicator can be used to dispense medication into a body cavity or onto the skin of a human or an animal. One specific application for a medicinal applicator is to dispense medication, such as a yeast infection medication, into a woman's vagina. The curl can be inwardly or outwardly extending. The outwardly extending curl can serve as a fingergrip ring to aid in holding the applicator relative to a woman's vagina.

The tubular member 12 can be of any desired length. However, when used as a tampon applicator or as a medicinal applicator, the tubular member 12 should have a length of between about 1 inch to about 12 inches (about 25.4 mm to about 305 mm) and, preferably, between about 2 inches to about 6 inches (about 50.8 mm to about 152.7 mm). The most preferred length for a tampon applicator is about 3 inches (76.2 mm) and the most preferred length for a medicinal applicator, used to dispense a yeast infection medication, is about 6 inches (about 152.4 mm).

The tubular member 12 can be constructed of any kind of material. For use as a tampon applicator or as a medicinal applicator, the tubular member 12 should be constructed of paper, paperboard, cardboard, plastic, thermoplastic film or a combination of such materials. The tubular member 12 can also be formed as a laminate consisting of at least two separate layers. Each layer can be of a similar or different material. It is also anticipated that the outer layer of the tubular member 12 can be coated with a suitable coating to give it a certain characteristic. For example, the coating can be used to give the applicator a smooth, slippery, water-permeable or water-impermeable characteristic.

If two or more layers are utilized to form the tubular member 12, they can be bonded together by an adhesive, such as glue, by heat and/or pressure, by ultrasonics or by any other known means.

The apparatus 10 for forming a curl on a tubular member 12 is especially useful when the tubular member 12 has an outside diameter of less than about 1.25 inches (about 31.7 mm), preferably, less than about 1 inch (about 25.4 mm), and most preferably, less than about 0.75 inches (about 19.05 mm). A diameter as small as about 0.25 inches (about 6.35 mm) can be curled using this apparatus 10. Tubular members having such relatively small diameters can be obtained by convolutely winding, spirally winding, longitudinally seaming, extruding or, if plastic molding the material together. The apparatus 10 is also particularly useful in curling a tubular member 12 having a wall 16 with a thickness of less than about 0.125 inches (about 3.175 mm), preferably less than about 0.10 inches (about 2.54 mm) and, most preferably, less than about 0.05 inches (about 1.27 mm). Such wall thicknesses are typically used for tampon applicators and medicinal applicators, especially those constructed of paper, paperboard, cardboard, plastic, etc.

Referring again to FIGS. 1–4, the apparatus 10 includes a first member 18 and a second member 20. It is anticipated that one of the members 18 or 20 will be held stationary while the other member is rotated. For purposes of discussion, the first member 18 will be described as being held stationary while the second member 20 is rotated. However, one skilled in the art will recognize that the first member 18 can be made to rotate while the second member 20 is held stationary. Likewise, it is also possible to rotate both the first and second members, 18 and 20 respectively, at different speeds in order to form the curl. The rotational speed can vary between about 200 to about 5,000 rpm, preferably below about 2,000 rpm, and most preferably, between about 300 to about 1,800 rpm.

Figure 1:
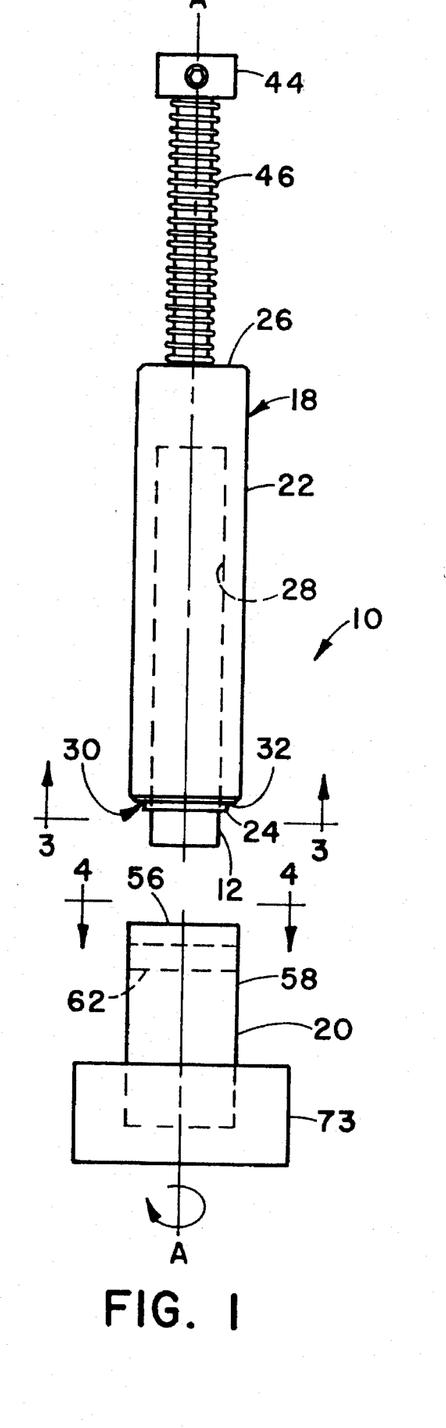
FIG. 1 is a side view of an apparatus for forming an outwardly directed curl on an end of a tubular member.
Figure 2:
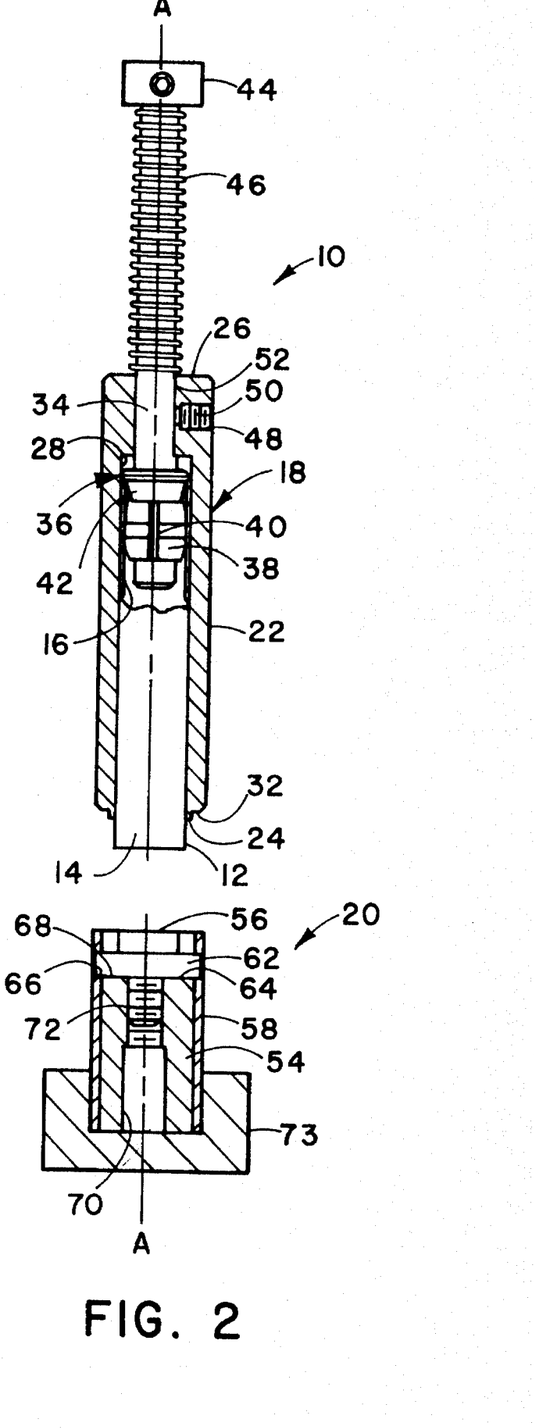
FIG. 2 is a cross-sectional view of an apparatus shown in FIG. 1.

The first member 18 is designed to hold the tubular member 12 stationary. The first member 18 is depicted as an elongated member having a central, longitudinal axis A—A. The first member 18 includes a housing 22 having first and second spaced apart ends, 24 and 26 respectively. The housing 22 also has an elongated bore 28 formed therethrough which is coaxially aligned with the central, longitudinal axis A—A. The bore 28 extends between the first and second ends 24 and 26 of the housing 22. The bore 28 is sized and configured to be capable of receiving the tubular member 12.

Extending axially outward from the first end 24 of the housing 22 is a shoulder 30. The shoulder 30 is depicted as an external shoulder having a circular cross-sectional profile and having an outer periphery 32. The outer periphery 32 is sized to mate with a portion of the second member 20. The thickness of the shoulder 30 is relatively thin although the specific thickness will vary depending upon the thickness of curl one desires to form. When the tubular member 12 is held in the first member 18, one end of the tubular member 12 will extend beyond the shoulder 30. This end of the tubular member 12 is the end which will be curled.

The first member 18 also includes a piston rod 34 which is partially situated in the bore 28. The piston rod 34 has a piston 36 attached to an end thereof which is located in the bore 28. The piston 36 includes a sleeve 38 having an outside diameter which is less than the inside diameter of the bore 28. The sleeve 38 contains an axially aligned slot 40 formed therethrough which enables the sleeve 38 to create a large enough diameter to produce a frictional fit with the tubular member 12. The piston 36 also has a conical surface 42 positioned inward from the sleeve 38 which acts as a stop for the tubular member 12. The conical surface 42 functions to axially align the tubular member 12 in the bore 28. The tubular member 12 contacts the piston 36 and the inside surface of the bore 28. In this position, the tubular member 12 will be held stationary by the frictional contact with the sleeve 38.

The opposite end of the piston rod 34 terminates in an enlarged head 44. Surrounding the piston rod 34 between the head 44 and the second end 26 of the housing 22 is a spring 46. The purpose of the spring 46 is to bias the piston rod 34 outward so that the piston 36 is positioned away from the first end 24 of the housing 22. This position permits the tubular member 12 to be placed in the bore 28 with only a predetermined amount extending out beyond the shoulder 30. It should be mentioned that although the spring 46 is taught as the biasing means, one skilled in the art may wish to use some other biasing mechanism, such as an electric, hydraulic or pneumatic member.

After a curl has been formed on an end of the tubular member 12, the tubular member 12 can be removed from the bore 28 by pushing the piston rod 34 downward or inward into the bore 28. As the piston rod 34 is pushed downward, the spring 46 will become compressed. As the piston rod 34 and the piston 36 are moved toward the first end 24 of the housing 22, the tubular member 12 will be displaced from the bore 28. With a majority of the tubular member 12 cleared from the bore 28, the tubular member 12 can be manually removed from the sleeve 38. Once the tubular member 12 is fully removed from the piston 36, the compressed spring 46 will urge the piston rod 34 and the piston 36 back to their original position within the bore 28. The first member 18 will then be ready to accept another tubular member 12 which is to be curled.

The first member 18 further contains a threaded hole 48 aligned perpendicular to the central bore 28. The threaded hole 48 is designed to receive a set screw 50. The piston rod 34 has a flat surface 52 machined into it which extends along a major portion of it's length between the piston 36 and the enlarged head 44. The set screw 50 is threaded into the threaded hole 48 and contacts the flat surface 52. This action prevents rotation of the piston rod 34 relative to the housing 22. It should be noted that in some situations, the rotation of the piston rod 34 is not undesirable and therefore there will not be a need for the set screw 50.

The second member 20 of the apparatus 10 is coaxially aligned along the central, longitudinal axis A—A of the first member 18 and is movably relative to the first end 24 of the first member 18. For purposes of discussion only, the second member 20 will be described as being aligned vertically below the first member 18, although the members 18 and 20 could be positioned at some other orientation if desired.

The formation of either an outwardly directed curl or an inwardly directed curl will be dictated by the configuration of the first and second members, 18 and 20 respectively. The configuration needed on the second member 20 to form an outwardly directed curl on one end of the tubular member 12 will first be described. The configuration of the tooling needed to form an inwardly directed curl will be explained later.

The second member 20 is engageable with the end of the tubular member 12 which extends outward past the shoulder 30 when the tubular member 12 is held in the bore 28 of the first member 18. The second member 20 includes a pilot 54 which is depicted as a cylindrical member. The pilot 54 has a first end 56 of reduced outside diameter which is sized and configured to be inserted into the outwardly extending end of the tubular member 12. Preferably, the first end 56 has a circular cross-sectional profile with an outside diameter which is at least about 0.002 inches (about 0.05 mm) smaller than the inside diameter of the tubular member 12. The insertion of the first end 56 of the pilot 54 into the tubular member 12 will assure that the wall 16 of the tubular member 12 cannot curl inward as the first and second members, 18 and 20 respectively, contact one another. The first end 56 of the pilot 54 can be inserted into the tubular member 12 any desired amount. However, the first end 56 of the pilot 54 should be inserted a distance of at least about 0.125 inches (about 3.17 mm) or more into the tubular member 12.

Figure 5:
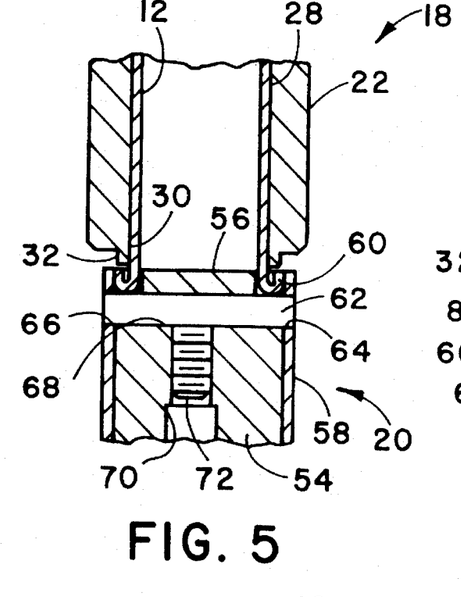
FIG. 5 is an enlarged view showing the interaction of the first and second members to form an outwardly extending curl on one end of the tubular member.

Referring to FIG. 5, the second member 20 also includes a sleeve 58 which surrounds the pilot 54. The sleeve 58 has an inside diameter which is in contact with the outer diameter of the pilot 54 except near the first end 56. At the first end 56 of the pilot 54, the inside diameter of the sleeve 58 is spaced apart from the outer diameter of the first end 56 of the pilot 54. This clearance establishes an open area around the outer circumference of the tubular member 12 when the first and second members, 18 and 20 respectively, are moved into engagement. The open area provides a circumferential opening into which the outer end of the tubular member 12 can be curled outwardly relative to the central, longitudinal axis A—A.

The inner diameter of the sleeve 58 cooperates with the outer periphery 32 of the shoulder 30 to form a curling chamber 60 when the second member 20 engages an end of the tubular member 12. Preferably, the clearance between the inner diameter of the sleeve 58 and the outer periphery of the shoulder 30 is between about 0.001 inches to about 0.005 inches (about 0.02 mm to about 0.127 mm). The sleeve 58 and pilot 54 are stationary relative to one another and are designed to move axially together.

Figure 7:
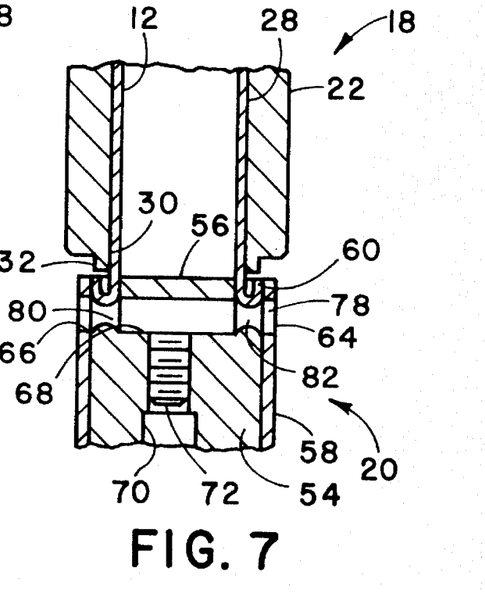
FIG. 7 is an enlarged view showing the interaction of the first and second members to form an outwardly extending curl on one end of the tubular member.

The second member 20 further includes a curling element 62 positioned through the pilot 54 and the sleeve 58 which is designed to contact the outwardly extending end of the tubular member 12 and form a curl thereon. The curling element 62 can be in the form of an elongated pin or cylindrically shaped member. The curling element 62 can be a solid or hollow member. The curling element 62 can also have a uniform outside diameter, as shown in FIG. 5, or a non-uniform outside diameter as depicted in FIG. 7. The curling element 62 is inserted through and retained in two transversely oriented apertures 64 and 66 formed in the sleeve 58 as well as a transversely oriented aperture 68 formed through the first end 56 of the pilot 54. The curling element 62 can be spaced vertically away from the first end 56 of the pilot 54 by a distance of at least about 1/16 of an inch (about 1.58 mm). The exact distance which the curling element 62 is spaced away from the first end 56 of the pilot 54 can vary.

The pilot 54 also has a central passageway 70 formed therein which is aligned along the central, longitudinal axis A—A. At least a portion of the passageway 70 is threaded to receive a set screw 72. The set screw 72 is designed to contact the curling element 62 and prevent it from rotating. It has been found that a better looking and more functional curl can be obtained when the curling element 62 is held stationary. However, for some applications, one may find that the curling element 62 can move or rotate without affecting the final appearance of the finished curl.

The second member 20 is designed to be inserted into a rotatable chuck 73 and can be rotated at a predetermined speed. The speed can vary depending upon the type of material the tubular member 12 is constructed of. The second member 20 is rotated while the first and second members, 18 and 20 respectively, are moved axially relative to one another. The first and second members, 18 and 20 respectively, can be reciprocally mounted relative to one another and timed to produce an automated setup. The speed at which the first and second members, 18 and 20 respectively, will engage can be controlled. It should be noted that the first and second members, 18 and 20 respectively, will approach one another and slidably contact each other without actual abutment. Actual contact and engagement occurs between the second member 20 and the end of the tubular member 12. The engagement of the first and second members, 18 and 20 respectively, causes the curling element 62 to contact the end of the tubular member 12 and form a curl thereon. The curl will be limited to the confines of the curling chamber 60.

Figure 3:
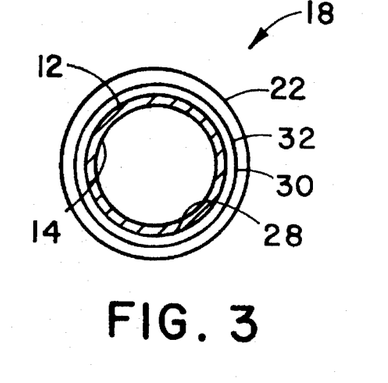
FIG. 3 is an end view of the first member taken along line 3—3 of FIG. 1.
Figure 4:
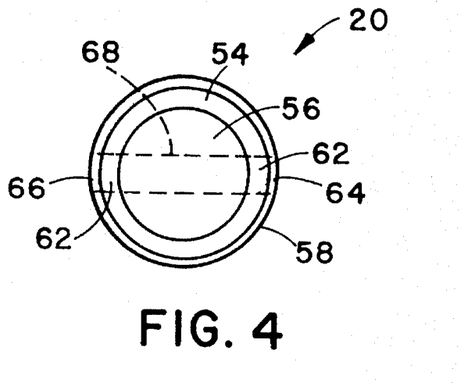
FIG. 4 is an end view of the second member taken along line 4—4 of FIG. 1.

The curling element 62 is designed to contact the exposed circumference of the tubular member 12. When the tubular member 12 is a cylindrical tube, the circumference is a complete 360° as depicted in FIG. 3. The curling element 62, see FIG. 4, is designed to contact this circumferential surface at two separate and distinct locations which are preferably approximately 180° apart. This arrangement permits the curling element 62 to contact less than about 50°, preferably less than 40°, and most preferably, less than about 30° of the circumference of the tubular member 12 at any time. This is important because this feature minimizes the buildup of frictional energy and allows a small diameter tubular member 12 to be curled without tearing or destroying the material from which it is constructed. If the curling element 62 contacted the entire circumference of the tubular member 12 simultaneously, frictional forces would prevent the formation of an acceptable curl having a good visual appearance. It has been found that the higher frictional forces also tend to generate additional heat which can hinder the formation of a good quality curl.

It should be mentioned that the curling element 62 can be coated, hardened or plated to enhance its useful life and to form a better quality curl. One coating process which has provided good results is Magnaplate HMF™ which is a proprietary multi-step coating process that creates an extremely hard, mirror-smooth surface with a low coefficient of friction. The Magnaplate HMF™ process using an electroless nickel coating, which has been modified by adding polymers, work fine. The Magnaplate coating process is available from General Magnaplate Corp. having an office at 1331 Route 1, Linden, N.J. 07036.

The first and second members, 18 and 20 respectively, can be moved into cooperation with one another such that the second member 20 exerts a force on the end of the tubular member 12. This force can vary but it has been from experimentation that a force of approximately 0.5 to about 10 pounds is sufficient to curl a tubular member 12 formed from paper, paperboard, cardboard, etc. A greater force may be needed to form a curl on a tubular member constructed of plastic. Preferably, a force of less than about 5 pounds is adequate for curling an end of a small diameter paper tube, and most preferably, a force of about 3 pounds is sufficient.

Figure 6:
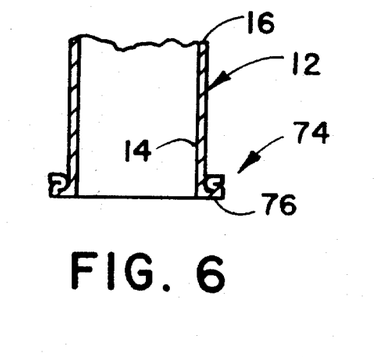
FIG. 6 is an enlarged view of a tubular member having an outwardly extending, integral curl formed on one end thereof using the curling element depicted in FIG. 5.

Referring to FIG. 6, the tubular member 12 is shown having an outwardly extending, integral curl 74 formed on one end thereof. This curl 74 is obtained by using the tooling depicted in FIG. 5. The curl 74 is referred to as an "s" curl having a square corner 76 because of it's shape. It has been found that when the curling element 62 has a uniform outer diameter, that the square corners are obtained.

Referring to FIG. 7, the first and second members, 18 and 20 respectively, are similar to those depicted in FIG. 5 except that the curling element 62 is replaced by a curling element 78 having a non-uniform outer diameter. The curling element 78 is an elongated, cylindrical pin having two spaced apart grooves 80 and 82 formed therein. Each groove 80 and 82 has a smaller outside diameter than the outside diameter of the remainder of the curling element 78. The grooves 80 and 82 are situated between the first end 56 of the pilot 54 and the sleeve 58. The grooves 80 and 82 are vertically aligned with the circumferential end of the tubular member 12 as well as with the radially outwardly situated curling chamber 60. The cross-sectional profile of each groove 80 and 82, depicted in FIG. 7, shows that each has a concave profile. Other cross-sectional profiles can also be utilized. These other cross-sectional profiles include square, rectangular, convex, semi-spherical, etc.

Figure 8:
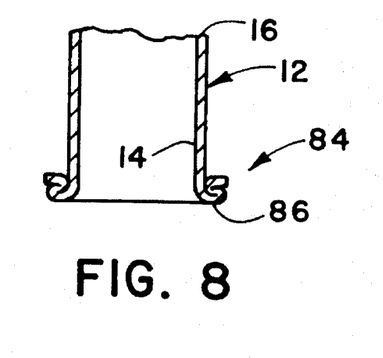
FIG. 8 is an enlarged view of a tubular member having an outwardly extending, integral curl formed on one end thereof using the curling element depicted in FIG. 7.

Referring to FIG. 8, the tubular member 12 is shown having an outwardly extending, integral curl 84 formed on one end thereof. This curl 84 is obtained by using the tooling depicted in FIG. 7. The curl 84 is referred to as an "s" curl having a rounded corner 86 because of it's shape. It has been found that when the curling element 78 has a non-uniform outer diameter, that the rounded corners 86 are obtained.

Figure 9:
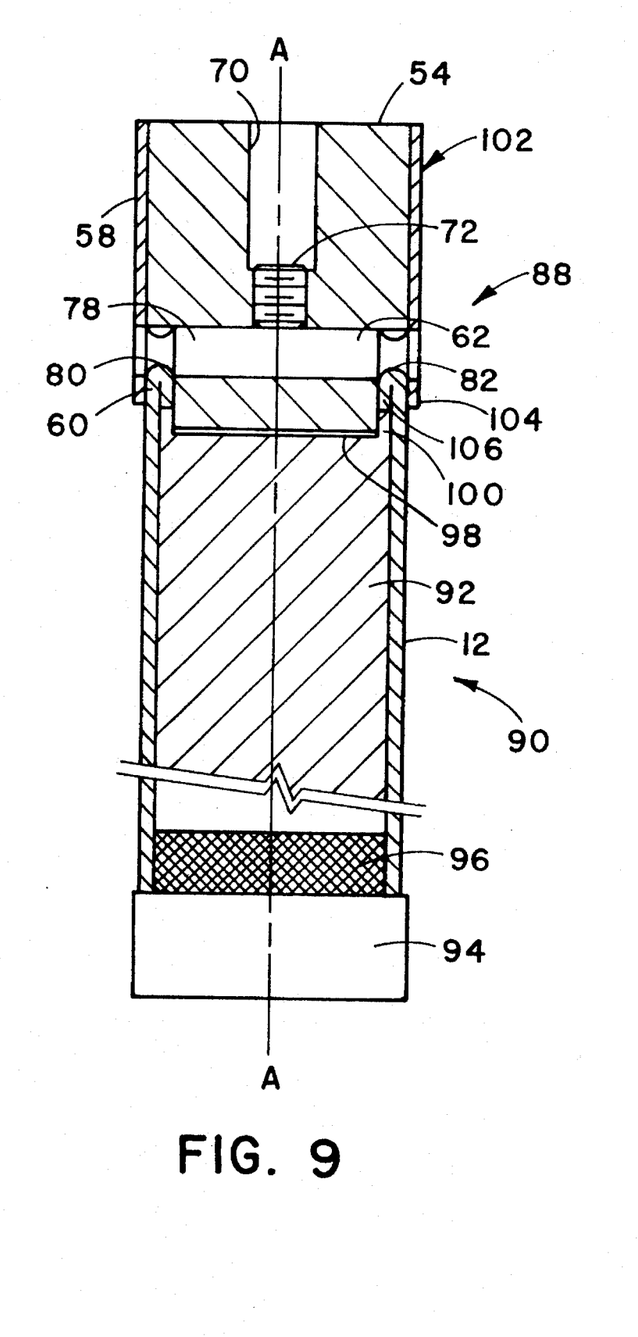
FIG. 9 is a cross-sectional view of an apparatus for forming an inwardly directed curl on an end of a tubular member.

Referring to FIG. 9, an apparatus 88 is shown for forming an inwardly directed, integral curl on an end of a tubular member 12. The apparatus includes a first member 90 which is capable of holding the tubular member 12 stationary. The first member 90 has an elongated central shaft 92 extending axially outward from an enlarged base 94. The diameter of the shaft 92 is sized to closely match the inside diameter of the tubular member 12 which is to be curled. The shaft 92 is of sufficient length to allow the tubular member 12 to be inserted over it and held in a desired position. The shaft also has a knurled section 96 which will assist in holding the tubular member 12 stationary and limit rotation movement. The shaft 92 further has a first end 98 surrounded by an external shoulder 100. The shoulder 100 extends axially beyond the first end 98 and the tubular member 12 extends axially beyond the external shoulder 100 when fully inserted onto the shaft 92. The amount which the tubular member 12 extends beyond the shoulder is predetermined depending upon how much curl is intended to be formed on the end thereof.

The apparatus 88 also includes a second member 102 which is coaxially aligned with and engageable with the first member 90. The second member 102 is constructed of the same parts as the second member 20, explained above. The only difference, other than size dimension, is that in the second member 102, the sleeve 58 has a surface 104 which is not aligned flush with the first end 56 of the pilot 54. This embodiment allows the first end 98 of the shaft 92 to engage the first end 56 of the pilot 54. When this occurs, the outer periphery of the first end 56 of the pilot 54 engages the inner periphery of the shoulder 100 and the curling chamber 60 is formed between the grooves 80 and 82 and the inner surface of the sleeve 58. The curling chamber 60 permits the end of the tubular member 12 to have an inwardly directed curl 106 to be formed thereon as the first and second members, 90 and 102 respectively, engage one another.

It has been found that when forming the inwardly directed curl 106, that a better quality curl can be obtained when the curling element 78, having a non-uniform diameter, is used. However, the material from which the tubular member 12 is constructed, it's wall thickness, it's diameter, the type of curl, etc. all contribute the final quality of the formed curl.

As stated above, either the first or second members, 90 and 102 respectively, can be rotated and either can be reciprocated toward and away from the other member. Furthermore, the apparatus 88 can include removal means for removing the tubular member 12 from the shaft 92. The removal means can be similar to that described and depicted above in FIGS. 1 and 2 or it can be some other mechanism, such as a pneumatic, hydraulic, electrical or electro-mechanical mechanism.

Figure 10:
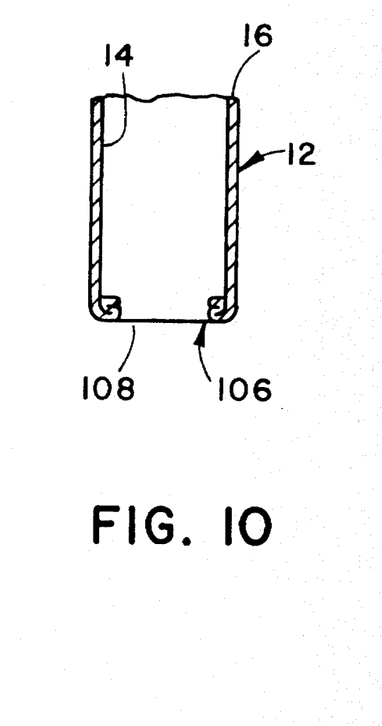
FIG. 10 is an enlarged view of a tubular member having an inwardly extending, integral curl formed on one end thereof using the curling element depicted in FIG. 9.

Referring to FIG. 10, the tubular member 12 is shown having an inwardly extending, integral curl 106 formed on one end thereof. This curl 106 is obtained by using the tooling depicted in FIG. 9. The curl 106 is referred to as an "s" curl having a rounded corner 108 because of it's shape. It has been found that when the curling element 78 has a non-uniform outer diameter, that the rounded corners 108 are obtained.

It should also be mentioned that formation of the curls 74 and 84 can be enhanced by adding some moisture to the paper tube. The addition of as little as 0.05 percent moisture is beneficial. Also, the addition of a wax to the end of the tubular member 12 which is to be curled will enhance the finished curl. Lastly, it is possible to heat set the curl 74 and 84 for a predetermined period of time to assure that it retains its shape and to increase it ability to keep it's shape under load. A heat set in the range of about 200° F. to about 400° F. for a time period of between about 1 second to about 10 seconds works well. An adequate heat set for a curl integrally formed on a tubular member constructed of at least two layers of paper can be obtained by heating the curl to about 300° F. for about 3 seconds. Any temperature below the burn melting temperature of the material from which the tubular member 12 is constructed may work provided the time period is adjusted to prevent destruction of the tubular member 12 itself.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An apparatus for forming a curl on a first end of a tubular member, comprising:

a) a first member capable of holding said tubular member and having a shoulder beyond which said first end of said tubular member extends;

b) a second member coaxially aligned with and engageable with said first end of said tubular member, said second member including a pilot sized to be inserted into said first end of said tubular member, a sleeve surrounding said pilot which cooperates with said shoulder when said second member engages said first end of said tubular member to form a curling chamber, and a curling element positioned between said pilot and said sleeve which is capable of contacting said first end of said tubular member; and c) means for rotating one of said members and moving said members into engagement, said engagement causing said curling element to contact said first end of said tubular member and form a curl thereon within the confines of said curling chamber.

2. The apparatus of claim 1 wherein said first member is held stationary and said second member is rotated.

3. The apparatus of claim 2 wherein said second member is reciprocally movable relative to said first member.

4. The apparatus of claim 1 wherein said second member is held stationary and said first member is rotated.

5. The apparatus of claim 4 wherein said first member is reciprocally movable relative to said second member.

6. The apparatus of claim 1 wherein said curling element is held stationary in an aperture formed through said pilot and said sleeve.

7. The apparatus of claim 1 wherein said first end of said tubular member contains a circumference of 360 degrees and said curling element contacts said circumference at two separate locations.

8. The apparatus of claim 7 wherein said two separate locations are spaced approximately 180 degrees apart.

9. The apparatus of claim 7 wherein said curling element contacts less than about 50 degrees of said circumference at any time.

10. The apparatus of claim 9 wherein said curling element contacts less than about 40 degrees of said circumference at any time.

11. The apparatus of claim 10 wherein said curling element contacts less than about 30 degrees of said circumference at any time.

12. An apparatus for forming an integral curl on a first end of a tubular member, comprising:

a) a first member capable of holding said tubular member stationary, said first member having an external shoulder beyond which said first end of said tubular member extends a set amount, said external shoulder having an outer periphery;

b) a second member coaxially aligned with and engageable with said first end of said tubular member, said second member including a pilot sized to be inserted into said first end of said tubular member, a sleeve surrounding said pilot which is mateable with said outer periphery of said external shoulder when said second member engages said first end of said tubular member to form a curling chamber, and a curling element positioned between said pilot and said sleeve which is capable of contacting said first end of said tubular member; and c) means for rotating said second member and moving said members into engagement at a predetermined speed, said engagement causing said curling element to contact said first end of said tubular member and form a curl thereon within the confines of said curling chamber.

13. The apparatus of claim 12 wherein said curling element is a pin having a non-uniform outside diameter.

14. The apparatus of claim 12 wherein said curling element contains a pair of spaced apart concave surfaces which contact said first end of said tubular member.

15. The apparatus of claim 12 wherein said first end of said tubular member contains a circumference of 360 degrees and said curling element contacts the circumference at two separate locations which are spaced approximately 180 degrees apart.

16. An apparatus for forming an outwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which is mateable with said external shoulder when said second member engages said first end of said tubular member to form a curling chamber, and a curling element transversely aligned between said pilot and said sleeve which is capable of contacting said first end of said tubular member;

c) means for rotating one of said members; and d) means for moving said members into engagement causing said curling element to contact said first end of said tubular member and form an outwardly extending curl thereon within the confines of said curling chamber.

17. The apparatus of claim 16 wherein said first member includes an elongated central cavity which is sized to receive said tubular member.

18. The apparatus of claim 16 wherein said first member includes means for removing said tubular member from said cavity.

19. The apparatus of claim 16 wherein said first end of said tubular member contains a circumference of 360 degrees and said curling element contacts said circumference at two separate locations simultaneously and the contact area is less than about 50 degrees of said circumference at any time.

20. The apparatus of claim 16 wherein said pilot is inserted into said first end of said tubular member at least 0.125 inches.

21. An apparatus for forming an integral curl on a first end of a tubular member, comprising:
   a) a first member capable of holding said tubular member stationary, said first member having an external shoulder beyond which said first end of said tubular member extends a set amount;
   b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element positioned between said pilot and said sleeve which is capable of contacting said first end of said tubular member; and
   c) means for rotating said second member and moving said members into engagement at a predetermined speed, said engagement causing said curling element to contact said first end of said tubular member and form a curl thereon within the confines of said curling chamber.

22. An apparatus for forming an inwardly extending, integral curl on a first end of a tubular member, comprising:
   a) a first member capable of holding said tubular member, said first member having an external shoulder beyond which said first end of said tubular member extends a set amount;
   b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element transversely aligned between said pilot and said sleeve which is capable of contacting said first end of said tubular member;
   c) means for rotating one of said members; and
   d) means for moving said members into engagement causing said curling element to contact said first end of said tubular member and form an inwardly extending curl thereon within the confines of said curling chamber.

23. The apparatus of claim 22 wherein said first member includes an elongated central shaft which is sized to receive said tubular member.

24. The apparatus of claim 22 wherein said first member includes means for removing said tubular member from said shaft.

25. An apparatus for forming a curl on a first end of a tubular member, comprising:
   a) a first member capable of holding said tubular member and having a shoulder beyond which said first end of said tubular member extends;
   b) a second member coaxially aligned with and engageable with said first end of said tubular member, said second member including a pilot sized to be inserted into said first end of said tubular member, a sleeve surrounding said pilot which cooperates with said shoulder when said second member engages said first end of said tubular member to form a curling chamber, and a curling element positioned between said pilot and said sleeve which is capable of contacting said first end of said tubular member, said curling element being a pin having a uniform outside diameter; and
   c) means for rotating one of said members and moving said members into engagement, said engagement causing said curling element to contact said first end of said tubular member and form a curl thereon within the confines of said curling chamber.

26. An apparatus for forming a curl on a first end of a tubular member, comprising:
   a) a first member capable of holding said tubular member and having a shoulder beyond which said first end of said tubular member extends;
   b) a second member coaxially aligned with and engageable with said first end of said tubular member, said second member including a pilot sized to be inserted into said first end of said tubular member, a sleeve surrounding said pilot which cooperates with said shoulder when said second member engages said first end of said tubular member to form a curling chamber, and a curling element positioned between said pilot and said sleeve which is capable of contacting said first end of said tubular member, said curling element being a cylindrically shaped stationary member; and
   c) means for rotating one of said members and moving said members into engagement, said engagement causing said curling element to contact said first end of said tubular member and form a curl thereon within the confines of said curling chamber.

27. An apparatus for forming a curl on a first end of a tubular member, comprising:
   a) a first member capable of holding said tubular member and having a shoulder beyond which said first end of said tubular member extends;
   b) a second member coaxially aligned with and engageable with said first end of said tubular member, said second member including a pilot sized to be inserted into said first end of said tubular member, a sleeve surrounding said pilot which cooperates with said shoulder when said second member engages said first end of said tubular member to form a curling chamber, and a curling element positioned between said pilot and said sleeve, said curling element including a pair of spaced apart convex surfaces which contact said first end of said tubular member; and
   c) means for rotating one of said members and moving said members into engagement, said engagement causing said curling element to contact said first end of said tubular member and form a curl thereon within the confines of said curling chamber.

28. An apparatus for forming an integral curl on a first end of a tubular member, comprising:
   a) a first member capable of holding said tubular member stationary, said first member having an external shoulder beyond which said first end of said tubular member extends a set amount, said external shoulder having an outer periphery;

b) a second member coaxially aligned with and engageable with said first end of said tubular member, said second member including a pilot sized to be inserted into said first end of said tubular member, a sleeve surrounding said pilot which is mateable with said outer periphery of said external shoulder when said second member engages said first end of said tubular member to form a curling chamber, and a curling element positioned between said pilot and said sleeve which is capable of contacting said first end of said tubular member, said curling element being a pin having a uniform outside diameter; and c) means for rotating said second member and moving said members into engagement at a predetermined speed, said engagement causing said curling element to contact said first end of said tubular member and form a curl thereon within the confines of said curling chamber.

29. An apparatus for forming an integral curl on a first end of a tubular member, comprising:

a) a first member capable of holding said tubular member stationary, said first member having an external shoulder beyond which said first end of said tubular member extends a set amount, said external shoulder having an outer periphery;

b) a second member coaxially aligned with and engageable with said first end of said tubular member, said second member including a pilot sized to be inserted into said first end of said tubular member, a sleeve surrounding said pilot which is mateable with said outer periphery of said external shoulder when said second member engages said first end of said tubular member to form a curling chamber, and a curling element positioned between said pilot and said sleeve which is capable of contacting said first end of said tubular member, said curling element being a cylindrically shaped stationary member; and c) means for rotating said second member and moving said members into engagement at a predetermined speed, said engagement causing said curling element to contact said first end of said tubular member and form a curl thereon within the confines of said curling chamber.

30. An apparatus for forming an integral curl on a first end of a tubular member, comprising:

a) a first member capable of holding said tubular member stationary, said first member having an external shoulder beyond which said first end of said tubular member extends a set amount, said external shoulder having an outer periphery;

b) a second member coaxially aligned with and engageable with said first end of said tubular member, said second member including a pilot sized to be inserted into said first end of said tubular member, a sleeve surrounding said pilot which is mateable with said outer periphery of said external shoulder when said second member engages said first end of said tubular member to form a curling chamber, and a curling element positioned between said pilot and said sleeve, said curling element including a pair of spaced apart convex surfaces which contact said first end of said tubular member; and c) means for rotating said second member and moving said members into engagement at a predetermined speed, said engagement causing said curling element to contact said first end of said tubular member and form a curl thereon within the confines of said curling chamber.

31. An apparatus for forming an outwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which is mateable with said external shoulder when said second member engages said first end of said tubular member to form a curling chamber, and a curling element transversely aligned between said pilot and said sleeve which is capable of contacting said first end of said tubular member, said curling element being a pin having a uniform outside diameter;

c) means for rotating one of said members; and d) means for moving said members into engagement causing said curling element to contact said first end of said tubular member and form an outwardly extending curl thereon within the confines of said curling chamber.

32. An apparatus for forming an outwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which is mateable with said external shoulder when said second member engages said first end of said tubular member to form a curling chamber, and a curling element transversely aligned between said pilot and said sleeve which is capable of contacting said first end of said tubular member, said curling element being a a cylindrically shaped stationary member;

c) means for rotating one of said members; and d) means for moving said members into engagement causing said curling element to contact said first end of said tubular member and form an outwardly extending curl thereon within the confines of said curling chamber.

33. An apparatus for forming an outwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which is mateable with said external shoulder when said second member engages said first end of said tubular member to form a curling chamber, and a curling element transversely aligned between said pilot and said sleeve, said curling element including a pair of spaced apart convex surfaces which contact said first end of said tubular member;

c) means for rotating one of said members; and d) means for moving said members into engagement causing said curling element to contact said first end of said tubular member and form an outwardly extending curl thereon within the confines of said curling chamber.

34. An apparatus for forming an integral curl on a first end of a tubular member, comprising:

a) a first member capable of holding said tubular member stationary, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element positioned between said pilot and said sleeve which is capable of contacting said first end of said tubular member, said curling element being a pin having a uniform outside diameter; and c) means for rotating said second member and moving said members into engagement at a predetermined speed, said engagement causing said curling element to contact said first end of said tubular member and form a curl thereon within the confines of said curling chamber.

35. An apparatus for forming an integral curl on a first end of a tubular member, comprising:

a) a first member capable of holding said tubular member stationary, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element positioned between said pilot and said sleeve which is capable of contacting said first end of said tubular member, said curling element being a cylindrically shaped stationary member; and c) means for rotating said second member and moving said members into engagement at a predetermined speed, said engagement causing said curling element to contact said first end of said tubular member and form a curl thereon within the confines of said curling chamber.

36. An apparatus for forming an integral curl on a first end of a tubular member, comprising:

a) a first member capable of holding said tubular member stationary, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element positioned between said pilot and said sleeve, said curling element including a pair of spaced apart convex surfaces which contact said first end of said tubular member; and c) means for rotating said second member and moving said members into engagement at a predetermined speed, said engagement causing said curling element to contact said first end of said tubular member and form a curl thereon within the confines of said curling chamber.

37. An apparatus for forming an inwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element transversely aligned between said pilot and said sleeve which is capable of contacting said first end of said tubular member, said curling element being a pin having a uniform outside diameter;

c) means for rotating one of said members; and d) means for moving said members into engagement causing said curling element to contact said first end of said tubular member and form an inwardly extending curl thereon within the confines of said curling chamber.

38. An apparatus for forming an inwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element transversely aligned between said pilot and said sleeve which is capable of contacting said first end of said tubular member, said curling element being a cylindrically shaped stationary member;

c) means for rotating one of said members; and d) means for moving said members into engagement causing said curling element to contact said first end of said tubular member and form an inwardly extending curl thereon within the confines of said curling chamber.

39. An apparatus for forming an inwardly extending, integral curl on a first end of a tubular member, comprising:

a) a first member capable of holding said tubular member, said first member having an external shoulder beyond which said first end of said tubular member extends a set amount;

b) a second member coaxially aligned with and engageable with said first end of said tubular member, said second member including a pilot sized to be inserted into said first end of said tubular member, a sleeve surrounding said pilot which cooperates with said external shoulder when said second member engages said first end of said tubular member to form a curling chamber, and a curling element transversely aligned between said pilot and said sleeve, said curling element including a pair of spaced apart convex surfaces which contact said first end of said tubular member;

c) means for rotating one of said members; and d) means for moving said members into engagement causing said curling element to contact said first end of said tubular member and form an inwardly extending curl thereon within the confines of said curling chamber.

* * * * *